(12) United States Patent
Marchal et al.

(10) Patent No.: US 9,669,007 B2
(45) Date of Patent: Jun. 6, 2017

(54) METHOD FOR OBTAINING A STABLE GEL OF HYALURONIC ACID AND OF A FREE FORM OF VITAMIN C AND/OR A SALT THEREOF

(71) Applicant: AURIGA INTERNATIONAL, Waterloo (BE)

(72) Inventors: Alfred Marchal, Waterloo (BE); Jerome Cabou, Saint Aybert (FR); Damien Lacroix, Emage (BE); Jacques Dubois, Villers-la-Ville (BE)

(73) Assignee: Auriga International, Waterloo (BE)

( * ) Notice: Subject to any disclaimer, the term of this patent is extended or adjusted under 35 U.S.C. 154(b) by 0 days.

(21) Appl. No.: 14/786,721

(22) PCT Filed: Apr. 23, 2014

(86) PCT No.: PCT/EP2014/058229
§ 371 (c)(1),
(2) Date: Jan. 6, 2016

(87) PCT Pub. No.: WO2014/173941
PCT Pub. Date: Oct. 30, 2014

(65) Prior Publication Data
US 2016/0106707 A1    Apr. 21, 2016

(30) Foreign Application Priority Data
Apr. 26, 2013  (BE) .................................. 2013/0295

(51) Int. Cl.
| | | |
|---|---|---|
| *A61K 31/375* | (2006.01) | |
| *A61K 8/67* | (2006.01) | |
| *A61K 8/73* | (2006.01) | |
| *A61Q 19/08* | (2006.01) | |
| *A61K 9/00* | (2006.01) | |
| *A61K 8/04* | (2006.01) | |
| *A61K 8/19* | (2006.01) | |
| *A61K 8/23* | (2006.01) | |
| *A61K 31/728* | (2006.01) | |
| *A61K 47/02* | (2006.01) | |
| *A61K 9/06* | (2006.01) | |
| *A61K 45/06* | (2006.01) | |
| *A61K 47/36* | (2006.01) | |
| *A61Q 19/00* | (2006.01) | |

(52) U.S. Cl.
CPC ............ *A61K 31/375* (2013.01); *A61K 8/042* (2013.01); *A61K 8/19* (2013.01); *A61K 8/23* (2013.01); *A61K 8/676* (2013.01); *A61K 8/735* (2013.01); *A61K 9/0019* (2013.01); *A61K 9/06* (2013.01); *A61K 31/728* (2013.01); *A61K 45/06* (2013.01); *A61K 47/02* (2013.01); *A61K 47/36* (2013.01); *A61Q 19/00* (2013.01); *A61Q 19/08* (2013.01); *A61K 2800/52* (2013.01); *A61K 2800/592* (2013.01); *A61K 2800/74* (2013.01); *A61K 2800/805* (2013.01); *A61K 2800/91* (2013.01)

(58) Field of Classification Search
CPC .... A61K 31/375; A61K 31/728; A61K 8/042; A61K 8/19; A61K 8/23; A61K 8/676; A61K 8/735; A61K 45/06; A61K 47/02; A61K 47/36; A61K 2800/52; A61K 2800/592; A61K 2800/74; A61K 2800/805; A61K 2800/91; A61K 2800/95; A61Q 19/00; A61Q 19/08
See application file for complete search history.

(56) References Cited

U.S. PATENT DOCUMENTS

| | | | |
|---|---|---|---|
| 6,238,713 B1 * | 5/2001 | Von Rhein | ............ B65B 31/025 424/400 |
| 9,339,450 B2 | 5/2016 | Thorel et al. | |
| 2011/0172180 A1 | 7/2011 | Gousse et al. | |

FOREIGN PATENT DOCUMENTS

| | | | |
|---|---|---|---|
| DE | 102009008940 A1 | 8/2010 | |
| FR | 2948286 A1 | 1/2011 | |
| FR | WO 2011086458 A1 * | 7/2011 | ............. A61L 27/20 |
| WO | 02/15860 A1 | 2/2002 | |
| WO | 2011/086458 A1 | 7/2011 | |

OTHER PUBLICATIONS

International Search Report for PCT/EP2014/058229, mailed Nov. 20, 2014.

* cited by examiner

*Primary Examiner* — Sarah Pihonak
(74) *Attorney, Agent, or Firm* — McDonnell Boehnen Hulbert & Berghoff LLP

(57) ABSTRACT

The invention relates to a process for producing an aqueous gel comprising hyaluronic acid, vitamin C, and a stabilizing agent selected from the metabisulfites. According to the invention, such a process comprises the steps of a) preparing a mixture comprising crosslinked or non-crosslinked hyaluronic acid and/or a salt thereof with a molar mass of between 1000 Da and 10 MDa, from 0.1 to 20.0% by weight of vitamin C in its acid form, or its equivalent in ascorbate derived from a vitamin C salt, from 0.01 to 1.00% by weight of a stabilizing agent selected from the metabisulfites, and an aqueous solution added so that the hyaluronic acid content is between 0.01 and 100 mg/ml, so as to form a hydrogel, and b) degassing the mixture before the hydrogel being formed is completely swollen.

12 Claims, 2 Drawing Sheets

Figure 1:
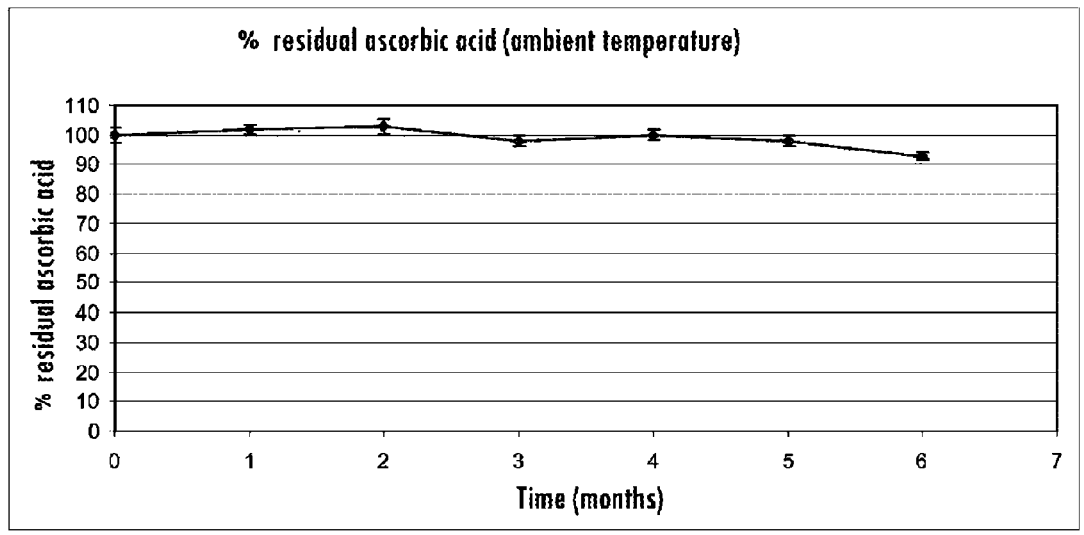

METHOD FOR OBTAINING A STABLE GEL OF HYALURONIC ACID AND OF A FREE FORM OF VITAMIN C AND/OR A SALT THEREOF

CROSS-REFERENCE TO RELATED APPLICATION

This application is a U.S. national phase of International Application No. PCT/EP2014/058229, filed Apr. 23, 2014, which claims priority to Belgium Patent Application No. 2013/0295, filed Apr. 26, 2013, the disclosures of which are hereby incorporated by reference in their entirety.

1. FIELD OF THE INVENTION

The invention relates to a process for obtaining an injectable aqueous composition of crosslinked or non-crosslinked hyaluronic acid or at least one salt thereof known as hyaluronate, and vitamin C or a salt thereof known as ascorbate, in the form of a stable hydrogel that can be stored without any notable deterioration for a period of several months and that is preferably not subject to yellowing. More particularly, the invention relates to an injectable aqueous composition of crosslinked or non-crosslinked hyaluronic acid or a salt thereof, and vitamin C in its acid form or its equivalent in ascorbate derived from a vitamin C salt, in the form of a hydrogel that can be obtained by this process.

The composition according to the invention can be used for aesthetic or therapeutic purposes.

2. PRIOR ART SOLUTIONS

Hyaluronic acid compositions are generally used in the form of an injectable gel. In aesthetic or reconstructive medicine, hyaluronic acid gel can be injected under the skin in order to fill wrinkles and fine lines, or to reshape the face or lips. These gels are also used in therapeutic medicine, and have applications in the field of ophthalmology in particular, in which the gel makes it possible to hydrate the eye and soothe the cornea after a cornea transplant or glaucoma or cataract surgery. The gel can also be injected into the joints in order to reduce joint pain, particularly in rheumatology.

These gels may be improved, particularly in terms of their duration of effect and resistance to deterioration in the body, through the use of additives.

These additives can also have complementary effects that enhance the effects of treatment by hyaluronic acid injection. Such additives can, for example, extend the duration of the desired effect, optimize the distribution of the injected product, limit pain during injection, and provide a complementary action, including anti-ecchymotic, antioxidant, and hyaluronic acid- or collagen-stimulating properties.

Of the various additives that can be used, L-ascorbic acid or vitamin C is particularly advantageous due to its antioxidant, anti-aging, and collagen-promoting properties.

However, it is known that combining vitamin C and/or a salt thereof in a free form—i.e. in acid form or in the form of an ascorbate derived from a vitamin C salt—with a hyaluronic acid gel does not make it possible to produce a gel that is sufficiently stable. In fact, the addition of vitamin C causes the deterioration of the hyaluronic acid and results in the liquefaction of the gel and the yellowing of the solution. This deterioration is particularly undesirable insofar as these compositions deteriorate quickly when they are heat-sterilized. Moreover, the vitamin C molecule itself is not very stable and deteriorates quickly. Such compositions are therefore not easy to produce, store for later use, or sterilize.

The deterioration of the hyaluronic acid gel and the vitamin C results in a significant loss in the viscosity and viscoelasticity of the gel, a sign of early deterioration prior to total breakdown into a liquid and the appearance of a deep yellow color.

There are stable compositions known from the documents US 2001/0171286, WO 2011/086458 and US 2012/0225842 that combine hyaluronic acid gels and ascorbic acid derivatives, possibly comprising an added stabilizer. However, such compositions are only stable when a vitamin C derivative is used, particularly magnesium or sodium ascorbyl phosphate or ascorbic acid-2 glucoside (AA2G). In fact, when vitamin C and/or a salt thereof is used in a free form, the hyaluronic gel deteriorates rapidly when the composition is sterilized in an autoclave. After treatment in an autoclave, the gel yellows and deteriorates. This deterioration of the hyaluronic acid is also known to the person skilled in the art. For example, the documents WO 95/29683 and FR 2 900 575 describe the stability problems of hyaluronic acid gels when they are combined with vitamin C or its salts in a free form.

Moreover, it is commonly accepted that the use of ascorbic acid esters, particularly the palmitate, or other vitamin C derivatives—for example fatty acid ascorbates, ascorbic acid-2 glucoside, or ascorbyl phosphate—provides less effectiveness than the direct use of vitamin C or its salts in a free form.

There is therefore a need for an injectable gel comprising hyaluronic acid and vitamin C and/or one of its salts in a free form that is stable enough to be heat-sterilized in an autoclave, i.e. so that the gel does not have any significant loss of viscosity and/or viscoelasticity, does not break down into a liquid form, and does not yellow.

3. OBJECTS OF THE INVENTION

A particular object of the invention is to overcome these drawbacks of the prior art.

More precisely, one object of the invention is to implement a process for obtaining an aqueous gel comprising crosslinked or non-crosslinked hyaluronic acid or a salt thereof known as hyaluronate, vitamin C in a free form and/or a salt thereof known as ascorbate, and a stabilizing agent selected from the metabisulfites.

Another object of the invention, in at least one of its embodiments, is to provide an aqueous gel comprising crosslinked or non-crosslinked hyaluronic acid or the corresponding hyaluronate, and a free form of vitamin C and/or a salt thereof known as ascorbate. The gel must be stable enough to be able to be sterilized in an autoclave and packaged in order to be stored for several months, preferably at least 6 months, without any notable deterioration of the gel or its components, particularly the vitamin C.

A further object of the invention, in at least one of its embodiments, is to combine the benefits of a hyaluronic acid injection with the antioxidant, anti-aging, and collagen-promoting effects of vitamin C and/or one of its salts, used in a free form.

A further object of the invention is the use in the cosmetic field of a formula containing a crosslinked or non-crosslinked hyaluronic acid in an acid or salt form, vitamin C and/or a salt thereof, particularly sodium ascorbate, in a free form, i.e. in the acid or ascorbate form, and a stabilizing agent selected from the metabisulfites.

Another object of the invention is the use for aesthetic, reconstructive, or therapeutic purposes of an injectable gel comprising crosslinked or non-crosslinked hyaluronic acid in acid or salt form, vitamin C or a salt thereof, particularly sodium ascorbate, in a free form, and a stabilizing agent selected from the metabisulfites.

4. DESCRIPTION OF THE INVENTION

According to a particular embodiment, the invention relates to a process for producing an aqueous gel comprising hyaluronic acid, vitamin C, and a stabilizing agent selected from the metabisulfites.

According to the invention, such a process comprises the following steps:

a) preparing a mixture comprising crosslinked or non-crosslinked hyaluronic acid and/or a salt thereof with a molar mass of between 1000 Da and 10 MDa, from 0.1 to 20.0% by weight of vitamin C in its acid form or its equivalent in ascorbate derived from a vitamin C salt, from 0.01 to 1.00% by weight of a stabilizing agent selected from the metabisulfites, and an aqueous solution added so that the hyaluronic acid content is between 0.01 and 100 mg/ml, in order to form a hydrogel.

b) degassing the mixture before the hydrogel being formed is completely swollen.

The general principle of the invention is based on the addition of a stabilizing agent selected from the metabisulfites, said addition being combined with a step for degassing the composition during the preparation of the gel. Surprisingly, the inventors found that the stability of the gel, i.e. a lack of deterioration for a period of at least 6 months or when treated in an autoclave, and the absence of any yellow coloration, are obtained when the addition of the stabilizing agent is combined with a step for degassing the composition during the preparation of the gel. Said stability corresponds to a stability of both the hyaluronic acid gel itself in terms of its viscoelastic properties and the vitamin C, the latter also resulting in an absence of yellowing of said gel.

A stabilizing agent is used in the composition of the gel. This stabilizing agent must be compatible with the medical or cosmetic applications, particularly for injections. Said agent is selected from the group of reducing agents or antioxidants, used at a concentration of between 0.01 and 1% by mass and preferably between 0.08 and 1%. This agent is selected from the metabisulfites, preferably from the alkaline and alkaline earth metabisulfites, more preferably from the alkaline metabisulfites, and most preferably from the potassium and sodium metabisulfites. The preferred stabilizing agent is sodium metabisulfite.

Thus, the invention is based on an entirely novel and inventive approach, combining the use of a stabilizing agent in the form of a metabisulfite with a degassing step. Essentially, while the addition of the stabilizing agent makes it possible to prevent the liquefaction of the gel, surprisingly, it does not make it possible to prevent the yellow coloration of the gel, even at high concentrations of stabilizing agent. For example, concentrations of between 0.08% by weight and 1& by weight of a stabilizing agent do not make it possible to prevent the yellow coloration of the gel. In order to prevent the yellow coloration of the hyaluronic acid gel, it is necessary to perform a degassing step during the preparation of the gel.

In particular, the inventors solved these deterioration and coloration problems by preparing a gelled aqueous composition comprising crosslinked or non-crosslinked hyaluronic acid or a salt thereof with a molar mass of between 1000 Da and 10 MDa ($10^7$ Da) and preferably between 50 KDa and 5 MDa, or more preferably between 200 KDa and 3 MDa, an excessively high molar mass making the gel difficult to handle while a molar mass below 1000 Da would make the composition too liquid. The gelled aqueous composition also comprises from 0.1 to 20.0% and preferably between 2 and 10% by weight of vitamin C, in its acid form or its equivalent in ascorbate derived from a vitamin C salt, from 0.01 to 1.00% and preferably between 0.08 and 1.00% by weight of a stabilizing agent selected from the metabisulfites, preferably from the alkaline and alkaline earth metabisulfites, more preferably from the alkaline metabisulfites, and most preferably from the sodium and potassium metabisulfites, the preferred stabilizing agent being sodium metabisulfite, and an aqueous solution added so that the hyaluronic acid content is between 0.01 an 100 mg/ml and preferably between 2 and 50 mg/ml.

The term hyaluronic acid will be used indistinguishably to describe cross-linked or non-crosslinked hyaluronic acid or the corresponding hyaluronate. Preferably, the hyaluronic acid salt is a sodium salt.

Depending on the desired applications, it is possible to use a mixture of cross-linked and non-crosslinked hyaluronic acids. In essence, cross-linked hyaluronic acid makes it possible to obtain higher viscosity and stability. Conversely, non-crosslinked hyaluronic acid makes it possible to obtain more fluid compositions. The cross-linking agents are preferably diols, which in particular may be selected from 1,4-butanediol diglycidyl ether, 1,4-bis(2,3-epoxypropoxy)butane, 1,4-bisglycidyloxybutane, 1,2-bis(2,3-epoxypropoxy)ethylene, and 1-(2,3-epoxypropyl)-2,3-epoxycyclohexane.

For these reasons, it can be advantageous to combine cross-linked and non-crosslinked hyaluronic acid in the manufacture of implants. Hyaluronic acid is sold under the trademarks Juvederm by Allergan or Restylane by Medicis Aesthetics.

The term vitamin C may be interpreted to cover the free forms of ascorbic acid, i.e. ascorbic acid in the form of levorotatory acid or a salt thereof known as ascorbate.

The aqueous phase used for the preparation of the hyaluronic acid gel may be selected by a person skilled in the art based on general knowledge, so as to be compatible with the applications of the injectable gel.

The injectable gel should preferably have a pH that is not too acid in order to be compatible with the various applications of the gel. The aqueous phase used according to the invention is preferably a buffered aqueous solution with a pH between about 5 and about 8. The aqueous phase may contain any useful additive that is known to the person skilled in the art and compatible with the application, for example in order to improve the gel, increase its resistance, or prevent pain during injection.

The words "degassing of the mixture before the hydrogel being formed is completely swollen" are intended to indicate the fact that the hyaluronic acid generally does not swell instantaneously. This means that between the mixing of the hyaluronic acid in the solid state with water and the obtainment of the viscous gel, there is a period of time during which it is easier to degas the solution before it becomes too viscous, given that the gel swells gradually by absorbing the surrounding water.

Advantageously, the process according to the invention is such that the mixture in step a) comprises from 2 to 10% by weight of vitamin C in acid form and/or in the form of at least one ascorbic acid salt, and from 0.08 to 1% by weight of a stabilizing agent selected from the metabisulfites.

Thus, surprisingly, the inventors observed that these ranges of concentration made it possible to obtain a satisfactory stabilizing effect.

According to a preferred or exemplary embodiment of the invention, the process according to the invention is such that during the mixing step a) the crosslinked or non-crosslinked hyaluronic acid and/or salt thereof, the vitamin C in acid form or its equivalent in ascorbate derived from a vitamin C salt, and the stabilizing agent selected from the metabisulfites are used in a solid form, then mixed with the aqueous solution.

This makes it possible to subsequently obtain a homogeneous gel and to facilitate the operation for degassing the mixture.

According to an alternative embodiment of the above, the process according to the invention is such that an aqueous solution comprising vitamin C in acid form, or its equivalent in ascorbate derived from a vitamin C salt, and the stabilizer selected from the metabisulfites is prepared in advance, then used to swell a previously prepared, partially swollen gel of crosslinked or non-crosslinked hyaluronic acid and/or a salt thereof. Alternatively, an aqueous solution of vitamin C in acid form or its equivalent in ascorbate derived from a vitamin C salt is prepared in advanced, then used to swell a previously prepared, partially swollen gel of crosslinked or non-crosslinked hyaluronic acid and/or a salt thereof comprising a stabilizer selected from the metabisulfites.

The words "partially swollen" are intended to indicate the fact that the hyaluronic acid gel can still "absorb" the aqueous phase added to form a gel of suitable viscoelasticity for the intended application without liquefying, dispersing or resulting in the appearance of a supernatant.

This makes it possible to subsequently obtain a homogeneous gel and to facilitate the operation for degassing the mixture.

These two alternative embodiments, or any process combining these two alternatives, make it possible to obtain a homogeneous hyaluronic acid gel and to facilitate the subsequent degassing of the mixture.

In order to avoid any problem linked to a too-fast swelling of the gel, it is advantageous to degas each of the preparations, i.e. the aqueous phase and the hyaluronic acid when the latter is used under the form of a partially swollen gel, as well as the solid-containing volume, then to perform the mixing under an inert and controlled atmosphere.

According to an advantageous embodiment, the process according to the invention is such that the degassing step is performed using ultrasound and/or alternating cycles of aspiration and addition of an inert gas, preferably alternating cycles of aspiration and addition of nitrogen.

According to an advantageous embodiment, the process according to the invention is such that a base, preferably a carbonate or bicarbonate, more preferably a bicarbonate, and most preferably sodium bicarbonate, is added to the mixture.

Thus, the addition of a base such as a carbonate or bicarbonate, preferably a bicarbonate, into the mixture comprising the vitamin C makes it possible to form the corresponding ascorbate in situ. Furthermore, combining a bicarbonate or carbonate, preferably a bicarbonate, and an acid in an aqueous solution triggers a release of carbon dioxide, which improves the degassing of the composition.

It is then advantageous to use an ascorbic acid salt such as a sodium salt. This salt can be added as is or formed in situ through the addition of a base such as sodium bicarbonate to ascorbic acid which, in the second case, enables the release of carbon dioxide during the acid/base reaction and also contributes to the degassing of the solution.

According to an advantageous embodiment, the process according to the invention is such that at least one additive selected from the group comprised of anesthetizing agents, anti-ecchymotic agents, agents that stimulate the production of hyaluronic acid, and agents that stimulate the production of collagen is added to the mixture.

Thus, using such additives makes it possible to limit the side effects linked to the injection of the gel according to the invention such as pain, ecchymosis, post-inflammatory hyperpigmentation, etc.

According to an advantageous implementation of the two preceding embodiments, the process according to the invention is such that during the mixing step a) the crosslinked or non-crosslinked hyaluronic acid and/or salt thereof, the vitamin C in acid form or its equivalent in ascorbate derived from a vitamin C salt, the stabilizing agent selected from the metabisulfites, and the carbonate or bicarbonate, preferably bicarbonate, are used in solid form, then mixed with the aqueous solution. Advantageously, the optional additive is also solid, unless the latter is already present in the gel or in the aqueous phase.

Thus, using solids for the preparation, more particularly in powder form, facilitates their handling, makes it easier to preserve unstable components such as vitamin C, which is stable in the solid state but not in solution, and also makes degassing easier.

According to an alternative implementation of the preceding embodiment, the process according to the invention is such that during the mixing step a) the aqueous solution is prepared in advance and comprises the vitamin C in acid form or its equivalent in ascorbate derived from a vitamin C salt, the stabilizing agent selected from the metabisulfites, the optional additive, and the bicarbonate; the aqueous solution is then used to swell a previously prepared, partially swollen gel of crosslinked or non-crosslinked hyaluronic acid and/or a salt thereof.

Thus, such an implementation makes it possible to avoid the use of hyaluronic acid in solid form in the case of an industrial process requiring equipment that cannot accommodate such use.

According to an advantageous embodiment, the process according to the invention is such that it comprises the following additional steps:

c) keeping the gel thus obtained in an inert atmosphere
d) allowing the gel to swell completely
e) sterilizing the gel.

According to an advantageous implementation of the preceding embodiment, the process according to the invention is such that it comprises an additional step f) for packaging the gel, said step f) being subsequent to step e) or occurring between steps d) and e); preferably, the additional step f) occurs between steps d) and e).

Thus, this embodiment enables the gel to be used and sold after packaging in sterile syringes.

According to an advantageous implementation of the preceding embodiment, the process according to the invention is such that the gel is sterilized in an autoclave.

Thus, this sterilization in an autoclave has the advantage of being less complex and easier to implement.

The process according to the invention makes it possible to obtain a gel that is stable enough to be sterilized in an autoclave and that is also stable over time, this property resulting in a gel that does not liquefy and does not yellow.

The gel obtained is compatible with injection, for example with a syringe, in the case of cosmetic and/or therapeutic applications.

It was also demonstrated that treating such a preparation in an autoclave has no significant effect on the concentration of vitamin C contained in the gel and accordingly, on its stability, said vitamin C not being deteriorated after sterilization and being stable over time.

The invention also relates to the gelled aqueous compositions that may be obtained by the process according to the invention. The inventors observed that surprisingly, the gelled aqueous compositions that may be obtained by the process according to the invention are stable enough to be sterilized by treatment in an autoclave and packaged so as to be stored for several months, preferably at least 6 months, without any notable deterioration of the gel or its components, particularly the vitamin C, which distinguishes them from the known compositions obtained by other processes.

In addition, the process relates to the use of such compositions as an injectable volumizing gel in aesthetic and reconstructive medicine, but also as an injectable gel for joint problems in rheumatology.

The injectable gels according to the invention can also contain additional ingredients, particularly anesthetic agents including lidocaine, anti-ecchymotic agents, agents that stimulate the production of hyaluronic acid, agents that stimulate cell proliferation, and/or agents that stimulate the production of collagen. To give a nonlimiting example, these additional agents for stimulating the production of collagen may be selected from the amino acids, particularly proline, glycine, hydroxyproline, lysine, and peptide derivatives obtained by amino acid coupling.

Finally, said gelled aqueous compositions are also packaged in syringes.

5. LIST OF THE FIGURES

FIG. 1: A graph illustrating the ascorbate content measured in the form of ascorbic acid after acidification of a hyaluronic acid gel stored at ambient temperature FIG. 2: A graph illustrating the ascorbate content measured in the form of ascorbic acid after acidification of a hyaluronic acid gel stored at 7° C.

Figure 3:
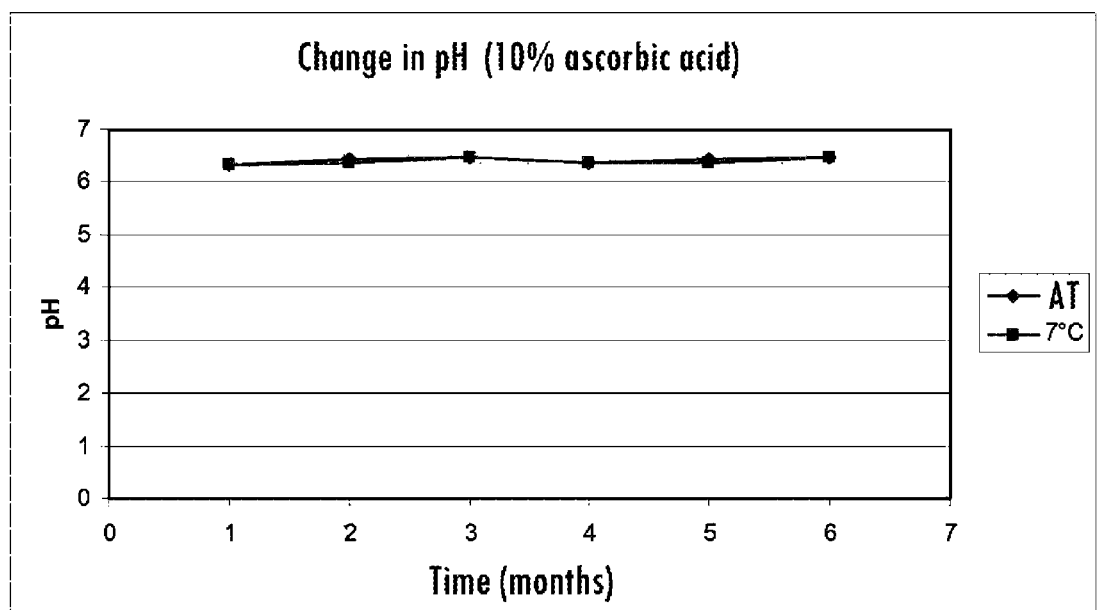

FIG. 3: A graph illustrating the pH evolution curves of hyaluronic acid gels supplemented with vitamin C according to the process of the invention as a function of time and at two different temperatures (7° C. and ambient temperature AT)

6. DESCRIPTION OF AT LEAST ONE EMBODIMENT OF THE INVENTION

It will be clear to the person skilled in the art that the present invention is not limited to the examples illustrated and described below. The invention comprises each of the novel characteristics individually as well as their combinations.

Stability Tests

A stability test was performed on a commercial gel for a period of 6 months. The samples were sterilized in an autoclave, then stored at a temperature of 7° C. and at ambient temperature for 6 months. The vitamin C content of the gel samples was analyzed by measuring the residual vitamin C. The appearance of the gel and its stability were also evaluated by visual observation of the organoleptic properties of the gel.

The characteristics of the gel were inspected visually in comparison to a control sample. The vitamin C content was measured by HPLC.

The tested batch was produced from a commercial monophasic hyaluronic acid gel, purified so as to no longer contain any solvents or additives such as lidocaine.

A quantity of sodium ascorbate equivalent to 10% by weight of vitamin C was generated in situ by adding at least a stoichiometric quantity of sodium bicarbonate to ascorbic acid; 0.08% by weight of sodium metabisulfite was added, as well as, lastly, the necessary quantity of water. The preparations were degassed using degassing processes known to the person skilled in the art, for example processes using ultrasound or the performance of vacuum/nitrogen cycles. The gel is then allowed to swell in a hermetically sealed container in a controlled atmosphere before the container is placed in an autoclave at a temperature of 121° C. for 15 minutes.

Example 1 (Comparative): Sterilization of a Crosslinked Gel Swelled without Addition of Vitamin C The contents of 5 syringes of commercial monophasic cross-linked monophasic gel are placed in a 25-ml Duran flask. The gel is sterilized in the autoclave at a temperature of 121° C. for 15 minutes.

The gel obtained after sterilization is translucent and colorless, and retains an appearance similar to what it had before treatment in the autoclave. The gel has not deteriorated due to the absence of vitamin C in the composition.

Example 2 (Comparative): Sterilization of a Hyaluronic Acid Gel with Addition of Vitamin C 0.5 g of ascorbic acid and 5 ml of water are placed in a 25-ml Duran flask. They are mixed until totally dissolved, after which 194 mg of hyaluronic acid (HA), obtained from a commercial source and pre-isolated in a solid form of solid purified HA, is added.

The flask containing the preparation is hermetically sealed and slowly agitated for 3 hours, then left at ambient temperature for 2 hours until the gel is completely swollen, then treated in the autoclave at 121° C. for 15 minutes in order to be sterilized.

After treatment in the autoclave, the gel has deteriorated into a clear solution with a pronounced yellow color.

Example 3: Sterilization of a Hyaluronic Acid Gel, with Addition of Vitamin C and Metabisulfite in the Solid Phase, without Performing a Degassing Step The gels are prepared as describe above, but without degassing.

| Example 3 | ascorbic acid | NaHCO$_3$ | Na$_2$S$_2$O$_5$ | Solid HA (*) | Water |
|---|---|---|---|---|---|
| Sample 1 | 1.0 g (10% m/v) | 0.5 g (5% m/v) | 8 mg (0.08% m/v) | 396 mg (3.96% m/v) | enough water to make 10 ml |
| Sample 2 | 0.5 g (10% m/v) | 0.25 g (5% m/v) | 50 mg (1% m/v) | 192 mg (3.84% m/v) | enough water to make 5 ml |

(*) HA: Hyaluronic acid; NaHCO$_3$: Sodium bicarbonate; Na$_2$S$_2$O$_5$: Sodium metabisulfite With 1% m/v corresponding to a mass concentration of 1 g per 100 ml.

In both cases, the gel retains its gel-like appearance without any significant visual difference in texture compared to the commercial gel. However, it has a yellow coloration after treatment in the autoclave.

Increasing the metabisulfite concentration by a factor of 12.5 between the two tests does not solve the problem.

Example 4 (Comparative): Sterilization of a Hyaluronic Acid Gel with Addition of Vitamin C, without Metabisulfite, with a Degassing Step

| Example 4 | Ascorbic acid | NaHCO$_3$ | Na$_2$S$_2$O$_5$ | Solid HA | Water |
|---|---|---|---|---|---|
| Quantities | 1.0 g | 0.5 g | — | 302 mg | 8.44 ml |
| % by weight | 9.76 | 4.88 | — | 2.95 | 82.41 |

1.0 g of ascorbic acid, 0.5 g of sodium bicarbonate and 302 mg of solid HA isolated from the commercial gel are placed in a 25-ml Duran flask. 8.44 ml of water is added and the flask is immediately sealed. A release of gas is observed as soon as the water is added. The flask is immediately sealed and left until the reagents have dissolved. The flask is briefly reopened twice in order to evacuate the excess pressure linked to the release of $CO_2$ and the degassing is continued using a known conventional process, after which the sample thus degassed and hermetically sealed is left to swell for a period of 2 hours at ambient temperature. The gel, once swollen, is sterilized in the autoclave at a temperature of 121° C. for a duration of 15 minutes.

After treatment in the autoclave, the gel retains its appearance without any visually significant difference in texture compared to the commercial gel. However, the gel has a yellow coloration.

Example 5 (Invention): Sterilization of a Hyaluronic Acid Gel with Addition of Vitamin C and Metabisulfite at a Concentration of 0.08% and Degassing Before Swelling and Treatment in the Autoclave

| Example 5 | Ascorbic acid | NaHCO$_3$ | Na$_2$S$_2$O$_5$ | Solid HA | Water |
|---|---|---|---|---|---|
| Quantities | 1.0 g | 0.5 g | 8.0 mg | 300 mg | 8.44 ml |
| % by weight | 9.76 | 4.88 | 0.08 | 2.93 | 82.36 |

1 g of ascorbic acid, 0.5 g of sodium bicarbonate, 8 mg of sodium metabisulfite and 300 mg of solid HA isolated from the commercial gel are placed in a 25-ml Duran flask. 8.44 ml of water is quickly added. A release of gas occurs as soon as the water is added. The flask is immediately sealed until the reagents have dissolved. The flask is briefly reopened twice in order to evacuate the excess pressure linked to the release of $CO_2$ and the degassing is continued using a conventional process, after which the sample thus degassed and hermetically sealed is left at ambient temperature until the gel is completely swollen, i.e. 4 hours in this case. The gel, once swollen, is sterilized in the autoclave at a temperature of 121° C. for a duration of 15 minutes.

After treatment in the autoclave, the gel retains its appearance, without any visually significant difference in texture compared to the commercial gel. The gel is also colorless and has no yellow coloration.

Example 6 (Invention): Stability of a Hyaluronic Acid Gel with Addition of Vitamin C and Metabisulfite and Degassing Before Treatment in an Autoclave Several gel samples were prepared as described in Example 5 and their stability was measured at ambient temperature and at 7° C.

After 6 months of storage in hermetically sealed flasks, the gels initially sterilized and stored at 7° C. or at ambient temperature, in both cases, remain stable and retain the appearance of a gel without any visually significant difference in texture compared to the initial gel and without the development of any yellow coloration.

Figure 2:
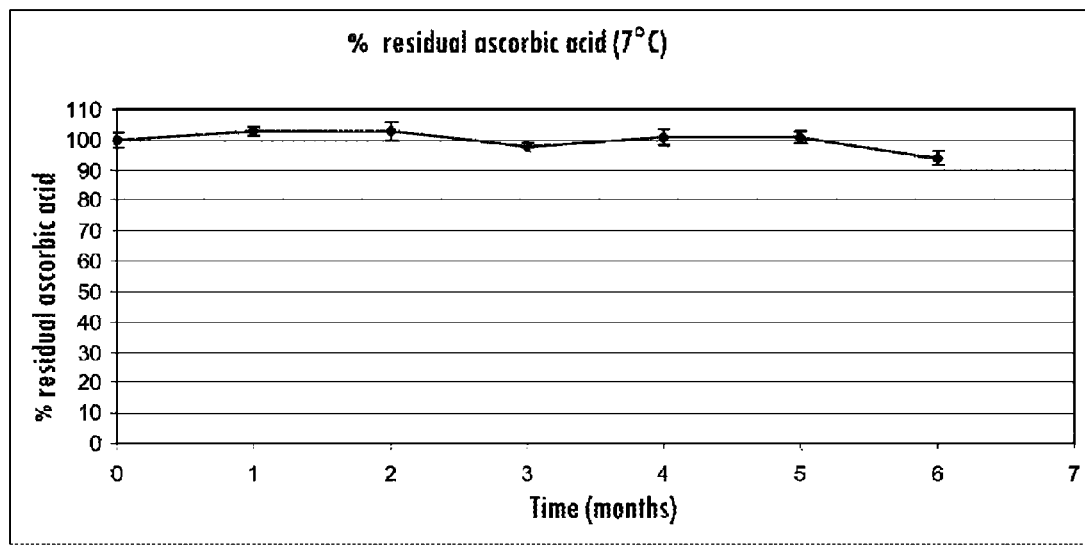

The ascorbate content measured in the form of ascorbic acid after acidification of the sample remains stable and confirms the stability of the active ingredient under these conditions (FIGS. 1 and 2).

Treatment in an autoclave does not cause any significant modifications in appearance or in the concentration of vitamin C.

The percentages of residual vitamin C are greater than 97% after 5 months of storage under both temperature conditions. However, a slight, not very significant decrease is observed during the last month, with a maximum variability of 3% linked to the process, with a residual percentage of around 93%.

It is noted that the pH of the gels does not change over a 6-month period, which demonstrates the stability of the active ingredients present in the gel (FIG. 3).

After 6 months, no qualitative change in appearance (color, viscosity, texture, etc.) is observed, and the pH has not changed significantly. The vitamin C concentration remains stable for the first 5 months, and seems to decrease very slightly over the course of the last month, reaching a residual rate after 6 months that is greater than 94% and 92%, at 7° C. and at ambient temperature, respectively.

The invention claimed is:

1. Process for producing an aqueous gel comprising hyaluronic acid, vitamin C, and a stabilizing agent selected from the metabisulfites, comprising the following steps:
   a. preparing a mixture comprising crosslinked or non-crosslinked hyaluronic acid and/or a salt thereof with a molar mass of between 1000 Da and 10 MDa, from 0.1 to 20.0% by weight of vitamin C in its acid form, or its equivalent in ascorbate derived from a vitamin C salt, from 0.01 to 1.00% by weight of a stabilizing agent selected from the metabisulfites, and an aqueous solution added so that the hyaluronic acid content is between 0.01 and 100 mg/ml, in order to form a hydrogel, and wherein the hydrogel optionally further comprises an additive or base;
   b. degassing the mixture before the hydrogel being formed is completely swollen.

2. Process according to claim 1, such that the mixture of step a) comprises from 2 to 10% by weight of vitamin C in acid form, or its equivalent in ascorbate derived from a vitamin C salt, and from 0.08 to 1% by weight of a stabilizing agent selected from the metabisulfites.

3. Process according to claim 1, such that during the mixing step a), the crosslinked or non-crosslinked hyaluronic acid and/or salt thereof, the vitamin C in its acid form or its equivalent in ascorbate derived from a vitamin C salt, and the stabilizing agent selected from the metabisulfites are used in a solid form, then mixed with the aqueous solution.

4. Process according to claim 1, such that an aqueous solution comprising vitamin C in acid form, or its equivalent in ascorbate derived from a vitamin C salt, and the stabilizer selected from the metabisulfites is prepared in advance, then used to swell a previously prepared, partially swollen gel of crosslinked or non-crosslinked hyaluronic acid and/or a salt thereof.

5. Process according to claim 1, such that the degassing step is performed using ultrasound and/or alternating cycles of aspiration and addition of an inert gas.

6. Process according to claim 1, such that a base is added to the mixture.

7. Process according to claim 1, further comprising that at least one additive selected from the group comprised of anesthetizing agents, anti-ecchymotic agents, agents that stimulate the production of hyaluronic acid, and agents that stimulate the production of collagen is added to the mixture.

8. Process according to claim 1, such that during the mixing step a), the crosslinked or non-crosslinked hyaluronic acid and/or salt thereof, the vitamin C in acid form or its equivalent in ascorbate derived from a vitamin C salt, the stabilizing agent selected from the metabisulfites, an optional additive, and a base selected from a carbonate or bicarbonate are used in solid form, then mixed with the aqueous solution.

9. Process according to claim 1, such that during the mixing step a), the aqueous solution is prepared in advance and comprises the vitamin C in acid form or its equivalent in ascorbate derived from a vitamin C salt, the stabilizing agent selected from the metabisulfites, an optional additive, and a base selected from a carbonate or bicarbonate; the aqueous solution is then used to swell a previously prepared, partially swollen gel of crosslinked or non-crosslinked hyaluronic acid and/or a salt thereof.

10. Process according to claim 1, such that it comprises the following additional steps:
   c. keeping the gel thus obtained in an inert atmosphere
   d. allowing the gel to swell completely
   e. sterilizing the gel.

11. Process according to claim 10, such that the gel is sterilized in an autoclave.

12. Process according to claim 6, such that the base added to the mixture is a carbonate or a bicarbonate.

* * * * *